United States Patent
Inouye et al.

(10) Patent No.: US 9,146,232 B2
(45) Date of Patent: Sep. 29, 2015

(54) METHOD FOR STABILIZING PROTEIN

(71) Applicant: JNC CORPORATION, Tokyo (JP)

(72) Inventors: Satoshi Inouye, Kanagawa (JP); Junichi Sato, Kanagawa (JP)

(73) Assignee: JNC Corporation, Tokyo (JP)

( * ) Notice: Subject to any disclaimer, the term of this patent is extended or adjusted under 35 U.S.C. 154(b) by 39 days.

(21) Appl. No.: 14/071,584

(22) Filed: Nov. 4, 2013

(65) Prior Publication Data

US 2014/0065727 A1 Mar. 6, 2014

Related U.S. Application Data

(62) Division of application No. 12/638,063, filed on Dec. 15, 2009, now abandoned.

(30) Foreign Application Priority Data

Dec. 19, 2008 (JP) ................................. 2008-323191

(51) Int. Cl.
*G01N 33/53* (2006.01)
*C07K 1/113* (2006.01)
*C07K 14/46* (2006.01)

(52) U.S. Cl.
CPC .............. *G01N 33/53* (2013.01); *C07K 1/1136* (2013.01); *C07K 14/461* (2013.01)

(58) Field of Classification Search
None
See application file for complete search history.

(56) References Cited

U.S. PATENT DOCUMENTS

| 6,346,276 | B1 * | 2/2002 | Tanouchi et al. | 424/523 |
| 6,572,883 | B1 * | 6/2003 | Eriksson | 424/451 |
| 6,709,669 | B1 * | 3/2004 | Murray et al. | 424/434 |
| 2005/0130262 | A1 * | 6/2005 | Lambolez et al. | 435/69.1 |
| 2005/0252072 | A1 * | 11/2005 | Cross et al. | 43/42 |
| 2006/0013828 | A1 * | 1/2006 | Kotler et al. | 424/199.1 |

FOREIGN PATENT DOCUMENTS

| DE | 150 544 | * | 9/1981 |
| JP | 56068607 A | * | 6/1981 |
| JP | H11-507819 | | 7/1999 |
| JP | 2000-507819 | | 6/2000 |
| JP | 200457196 A | * | 2/2004 |

OTHER PUBLICATIONS

Chisso Corporation, News, Scale Collagen Peptide [online]. Chisso Corporation, Dec. 21, 2004 [retrieved on Aug. 1, 2013 9:55:34 PM]. Retrieved from the Internet: <URL: <http://www.chisso.co.jp/english/news/041221.html>.*
JP 200457196 English translation produced by machine translation, Aug. 2, 2013.*

* cited by examiner

*Primary Examiner* — David Romeo
(74) *Attorney, Agent, or Firm* — Jianq Chyun IP Office

(57) ABSTRACT

An excellent protein stabilizer is provided, which has the following effects: (1) low probability with contamination of pathogens, (2) the effect of stabilization on photoproteins, and (3) minimization of loss of activity under lyophilizing conditions. A peptide from fish is used as the active ingredient for the protein stabilizer.

4 Claims, No Drawings

METHOD FOR STABILIZING PROTEIN

CROSS-REFERENCE TO RELATED APPLICATION

This application is a divisional application of and claims the priority benefit of U.S. application Ser. No. 12/638,063, filed on Dec. 15, 2009, now pending, which claims the priority benefit of Japan application serial no. 2008-323191, filed on Dec. 19, 2008. The entirety of each of the above-mentioned patent applications is hereby incorporated by reference herein and made a part of specification.

BACKGROUND OF THE INVENTION

1. Field of the Invention

The present invention generally relates to a protein stabilizer, a protein composition, a method for stabilizing a protein, and a kit containing a protein composition.

2. Description of Related Art

It is generally known that the function of a protein such as an enzyme is dependent on its higher order structure (or conformation). If its higher order structure is broken down for some reason, the original function may be lost or its catalytic activity may decrease. On the other hand, protein is mostly stored in a lyophilized form, and various lines of research have been performed to prevent loss of function and to preserve catalytic activity during the lyophilized process. For example, it is known that the following materials are useful as protein stabilizers: amino acids, such as sodium glutamate; proteins, such as albumin and skim milk; saccharides, such as sucrose and maltose; reducing agents, such as glutathione and mercaptoethanol; polyols, such as glycerol and sorbitol; and surfactants, such as Tween 80 and Brij 35.

As described above, amino acids, proteins, saccharides, reducing agents, polyols, and surfactants are well-known stabilizers for protein. In some cases, different combinations of amino acids, saccharides, reducing agents, polyols, and surfactants with a protein do not have sufficient effect on its stabilization. In contrast, bovine serum albumin is a protein stabilizer that does have sufficient ability to stabilize various proteins, and thus can be readily used as a protein stabilizer.

However, most of the proteins used for a protein stabilizer are obtained from quadrupeds such as cattle, and there is a possibility that the protein stabilizer will be contaminated with pathogens of the animals such as bovine spongiform encephalopathy (BSE) or foot-and-mouth disease. Therefore, a novel, safe and excellent protein stabilizer without contamination of pathogens is desired.

[Patent document 1] Japanese Patent Publication NO. 1985-280523.

[Patent document 2] Japanese Patent Publication NO. 1987-149628.

[Patent document 3] Japanese Patent Publication No. 2000-507819 (Japanese translation of PCT international application).

[Patent document 4] Japanese Patent No. 3343712.

SUMMARY OF THE INVENTION

The inventors have done extensive research to solve the problems in the prior art. It has been found that peptide from fish can significantly improve the stability of proteins, and the present invention has been established based on such knowledge.

The present invention provides:

(1) a protein stabilizer, containing a peptide from fish;

(2) the protein stabilizer of Item 1, in which the peptide from fish is a peptide prepared by hydrolyzing collagen or gelatin from fish;

(3) the protein stabilizer of Item 1 or 2, in which the weight-average molecular weight of the peptide from fish is in a range of 500-3,000;

(4) the protein stabilizer of any one of Items 1 to 3, in which the protein is a calcium-binding photoprotein;

(5) the protein stabilizer of Item 4, in which the calcium-binding photoprotein is selected from one or more of aequorin, obelin, clytin, mitrocomin, mineopsin, bervoin, and a variant thereof;

(6) a protein composition, containing the stabilizer of any one of Items 1 to 3 and a protein;

(7) the protein composition of Item 6, in which the weight ratio of the peptide from fish and the protein (peptide from fish/protein) is in a range of 10/1-10000/1;

(8) the protein composition of Item 6 or 7, in which the protein is a calcium-binding photoprotein;

(9) the protein composition of Item 8, in which the calcium-binding photoprotein is selected from one or more of aequorin, obelin, clytin, mitrocomin, mineopsin, bervoin, and a variant thereof;

(10) the protein composition of any one of Items 6 to 9, in which the protein composition is in the form of lyophilized powder;

(11) a method for stabilizing a protein, including allowing the protein stabilizer according to any one of Items 1 to 3 and the protein to be in the same system;

(12) the method for stabilizing a protein of Item 11, in which the protein is a calcium-binding photoprotein;

(13) the method for stabilizing a protein of Item 12, in which the calcium-binding photoprotein is selected from one or more of aequorin, obelin, clytin, mitrocomin, mineopsin, bervoin, and a variant thereof;

(14) a method for stabilizing a protein, including lyophilizing the protein composition of any one of Items 6 to 9; and

(15) a kit, including the protein composition of any one of Items 6 to 10.

Effect of the Invention

The protein stabilizer and the method for stabilizing a protein in the present invention have the following effects: (1) low probability of contamination with pathogens, (2) the effect of stabilization on photoproteins, and (3) minimization of loss of activity under lyophilizing conditions. As the protein stabilizer in the present invention has the effects described above, the protein composition containing the protein stabilizer and a protein not only can be used in research, but also can be reliably used for general consumption, as well as in toys or goods for relaxation.

DESCRIPTION OF THE EMBODIMENTS

The present invention will be described in detail below by reference to the following embodiments, but the present invention is not limited to these embodiments. Moreover, based on this description, the objects, features, advantages, and ideas of the present invention can be understood by those skilled in the art, such that the present invention can be easily implemented by those skilled in the art. The following aspects and embodiments of the invention are preferred aspects and embodiments, which are only for illustration and not for limitation. It is appreciated by those skilled in the art that, various modifications can be made from this description without departing from the spirit and scope of the present invention as disclosed in the specification.

1. Protein Stabilizer (1) Peptide from Fish

There is no specific limitation on the peptide that is applicable in the present invention, as long as the peptide is from fish. According to the present invention, the so-called peptide refers to a polypeptide that has a number of amino acids lower than 50 and can be obtained by hydrolyzing the proteins derived from fishes. The kind of fish is not particularly limited, and includes: sardine, saury, sparid, salmon, herring and carp. *Nemipterus virgatus* used as raw material of minced fish or *Myripristis berndti* or tilapia for fillet processing are large fish with large scales and can be used efficiently.

In the proteins of fish, proteins of muscles consisting of actin and myosin, collagen and elastin are dominant. The peptides used in the present invention are obtained by hydrolyzing from collagen and gelatin prepared by unwinding the triple helix structure of collagen, and have the advantage of ready availability, easy operation, and good useful effect. Furthermore, the collagen that is applicable for the invention can be obtained from any part of a fish, especially the scales, which contain large amounts of collagen and lower fat concentration, are preferred for collagen preparation.

The method for extracting collagen is not particularly limited and includes, for example, non-decalcification disclosed in Japanese Patent Publication No. 2004-57196, in which scales of fish are extracted with hot water, and then enzyme is added for hydrolysis. The method for extracting collagen also includes the method disclosed in Japanese Patent Publication No. 2004-91418, in which scales are decalcified with acid to get crude collagen, and then the crude collagen is hydrolyzed in an aqueous solution of a weak base, such as sodium bicarbonate, under pressurized conditions.

The hydrolyzing method is not particularly limited and includes, for example, acid degradation, enzyme degradation, and alkali degradation. Any method for obtaining the desired peptide can be adopted in the present invention.

Therefore, the essential ingredient of the present invention, i.e., peptide from fish, is not particularly limited, and the peptide can be easily prepared by hydrolyzing collagen or gelatin obtained from the scales of fishes and has high stabilization effect on proteins, especially the calcium-binding photoprotein described below, which is applicable to the present invention.

The weight-average molecular weight of the essential ingredient of the present invention, i.e., peptide from fish, is not particularly limited. However, if the weight average molecular weight of the essential ingredient is in the range of 100-10,000, and further, more significant or stable effect can be achieved in the range of 500-3,000. The weight-average molecular weight of the peptide can be determined by gel permeation chromatography (GPC). The equipment and determination conditions are as follows.

Pump unit: LC-10Ai (Shimadzu Corporation)
Column: Asahipak GF-1G 7B+Asahipak GF-510HQ+Asahipak GF-310HQ
Mobile phase: Acetonitrile/water (volume ratio)=45/55+0.1 v % trifluoroacetic acid
Flow rate: 0.5 ml/min
Column temperature: 40° C.
Ultraviolet (UV) detection condition: 215 nm
Injection volume: 10 μl The peptide from fish used in the present invention is commercially available and can be obtained easily. The peptide includes: Ixos HDL-50F (trade name, Nitta Gelatin), Fish Collagen WP (trade name, Maruha), Rousselot FGH (trade name, Rousselot), Marine Matrix (trade name, Yaizu), HACP-U2 (trade name, Jellice), Marine Collagen Oligo CF (trade name, Chisso).

The protein stabilizer of the present invention can be in any form of liquid, solid, and powder. If the protein stabilizer is in a liquid form, the preferred peptide from fish is dissolved or suspended in a buffer that pH 5.0-9.0. The buffer for use in the present invention includes: phosphate buffer, tris(hydroxymethyl)amino methane-HCl (Tris-HCl) buffer, Good buffer, HEPES buffer, citrate buffer, tetraborate buffer, succinate buffer, diethylbarbituric acid buffer, and MOPS buffer.

The protein stabilizer of the present invention can be merely composed of a peptide from fish, or also can further include other ingredients. The other ingredients can be any ingredients that have no adverse impact on the effect of the present invention, and include: flavor, preservative agent, reducing agent, chelating agent, salts, sugar, organic acid, amino acid, protein, surfactant, and organic solvent.

The weight percentage of the peptide from fish in the protein stabilizer is not particularly limited. The weight percentage of the peptide will vary due to the type, the amount of the protein to be combined or the degree of the effect desired. However, in order to perform a highly effective stabilizer, the weight percentage of the peptide is preferably higher than or equal to 0.01 wt %. Furthermore, as long as there is no adverse impact on the function of the protein and on the operation due to increase of viscosity, the weight percentage is preferably in the range of 0.01 wt %-10 wt %, more preferably in the range of 0.05 wt %-5 wt %, and most preferably in the range of 0.1 wt %-1 wt %. If the weight percentage is in the above-described ranges, significant stabilization effect can be achieved.

The types or weight percentages of the other ingredients are not particularly limited as long as there is no adverse impact on the effect of the present invention. The types or weight percentages of the other ingredients can be determined based on the type, the amount of the protein to be combined or the desired effect. The pH value of the protein stabilizer in the present invention is not particularly limited and can be chosen according to the type or function of the object of stabilization, i.e., the protein. For example, when the object, i.e., the protein, is a calcium-binding photoprotein, the pH value is preferably in the range of 5.0-9.0.

(2) Protein

The object of stabilization, i.e., the protein, is not particularly limited, and includes: enzymes, structural proteins, protein hormones, receptors, proteins related to intracellular signal, proteins consisting of muscles, such as actin or myosin, proteins as blood coagulation factors, casein, proteins having fluorescence activity, and proteins having luminescence activity.

However, no report has been found for a stabilizer that is effective for the calcium-binding photoprotein, and virtually, the stabilizer is limited to proteins from quadrupeds, such as bovine serum albumin (hereinafter called BSA). The stabilizer in the present invention has a significant effect on the stabilization of the calcium-binding photoprotein.

The calcium-binding photoprotein refers to a protein which emits light instantly upon specific binding with calcium ions, and includes, for example, aequorin, obelin, clytin, mitrocomin, mineopsin, bervoin, and a variant thereof. Among these, aequorin can be obtained at high purity and in a large amount; thus, aequorin is suitable for industrial use. Commercial aequorin is manufactured by Chisso Co., Ltd. or MP-Biomedicals Corporation. As for other calcium-binding photoproteins, the gene sequences are well known, and they can be prepared with known methods, such as the polymerase chain reaction (PCR) (Fagan, T F. et al., FEBS Lett. (1993) 333: 301-305, Japanese Patent Publication Nos. 2008-022848, WO 04/035620, WO 02/1591).

2. Protein Composition (1) Peptide from Fish

In the protein composition of the present invention, any one of the peptides from fish described above can be used in the present invention.

The ratio of the peptide from fish contained in the protein composition is not particularly limited, and the weight ratio of the peptide and the protein (peptide from fish/protein) is preferably in the range of 10/1-10000/1, and more preferably in the range of 100/1-1000/1. If the weight ratio is in the above ranges, the stabilization effect of the protein is significant.

(2) Protein

In the protein composition of the present invention, any one of the proteins described above can be used in the present invention. The protein can be used in any form of liquid, solid, or powder. When the protein is in a liquid form, the protein is preferably dissolved or suspended in a buffer that functions at pH 5.0-9.0. The applicable buffer in the present invention includes: phosphate buffer, Tris-HCl buffer, Good buffer, HEPES buffer, citrate buffer, tetraborate buffer, succinate buffer, diethylbarbituric acid buffer, and MOPS buffer.

(3) Third Ingredient

As long as there is no adverse impact on the effect of the present invention, a third ingredient can also be included in the protein composition of the present invention. The ingredient includes, for example, flavor, preservative agent, reducing agent, chelating agent, salts, sugar, organic acid, amino acid, protein, surfactant, and organic solvent.

As long as there is no adverse impact on the effect of the present invention, the weight ratio of the third ingredient in the composition is not particularly limited. The ratio can be determined according to the type or amount of the protein and the composition or amount of the protein stabilizer to be combined. The pH value of the composition is not particularly limited and can be suitably selected according to the type or function of the protein. For example, when the object, i.e., protein is a calcium-binding photoprotein, the pH value is preferably in the range of 5.0-9.0.

(4) Preparation of the Protein Composition

The protein composition of the present invention contains a peptide from fish and a protein to be stabilized, and the protein composition can be in any form of liquid, solid, or powder. Furthermore, the preparation method of the protein composition is not particularly limited, and can be appropriately selected according to the types or properties of the peptide from fish that is used and the protein to be stabilized.

As an example, when using a calcium-binding photoprotein, the preparation method of the protein composition includes: mixing a solution of the calcium-binding photoprotein with a solution of the peptide from fish, and then lyophilizing the mixed solution, which is described in detail below.

Furthermore, the so-called calcium-binding photoprotein, similar to the proteins described above, can be in any form of powder or liquid.

1) Solution of the Calcium-Binding Photoprotein

The solution of the calcium-binding photoprotein is prepared by dissolving or suspending the calcium-binding photoprotein in a buffer. The buffer is not particularly limited, and the buffer that functions at pH 5.0-9.0 is preferred. If the buffer is as described above, the luminescence activity of the calcium-binding photoprotein can be maximized. The buffer includes, for example, phosphate buffer, Tris-HCl buffer, Good buffer, HEPES buffer, citrate buffer, tetraborate buffer, succinate buffer, diethylbarbituric acid buffer, and MOPS buffer.

Furthermore, the solution of the calcium-binding photoprotein preferably contains a chelating agent to prevent contamination of calcium. The chelating agent can be any polydentate ligand that is capable of forming a chelate compound with calcium ion by coordination. The chelating agent includes, for example, ethylenediamine tetraacetic acid, hydroxyethylethylenediaminetriacetic acid, dihydroxyethylethylenediaminediacetic acid, trans-1,2-diaminocyclohexane-N,N,N',N'-tetraacetic acid, 1,3-propanediaminetetraacetic acid, diethylenetriaminepentaacetic acid, triethylenetetraminehexaacetic acid, nitrilotriacetic acid, sodium gluconate, hydroxyethyliminodiacetic acid, glycoletherdiaminetetraacetic acid, L-aspartic acid-N,N-diacetic acid, dicarboxymethylglutamic acid tetra-sodium salt, dihydroxyethylglycine, aminotrimethylenephosphonic acid, hydroxyethane phosphonic acid, and salts thereof.

Among the chelating agents, considering the stability constant of chelation with calcium, ethylenediamine tetraacetic acid, glycoletherdiaminetetraacetic acid, diethylenetriaminepentaacetic acid, trans-1,2-diaminocyclohexane-N,N,N',N'-tetraacetic acid, and salts thereof are preferred, and ethylenediamine tetraacetic acid and salts thereof (sometimes called EDTA) are especially preferred.

If there is no adverse impact on the luminescence activity, various salts, such as sodium chloride or ammonium sulphate can be included in the solution of the calcium-binding photoprotein.

The concentration of the protein in the solution of the calcium-binding photoprotein can be suitably determined according to the application. For example, for immunoassay, the protein, diluted to a concentration of 10 ng/ml-100 ng/ml, is applied.

Furthermore, for applications in the field of amusement or relaxation, if the concentration of the calcium-binding photoprotein is higher than or equal to 100 µg/ml, it can be visually confirmed whether the protein is luminescent, to be suitable for the intended use.

2) Solution of the Peptide from Fish

The solution of the peptide from fish can be prepared by dissolving or dispersing the peptide from fish in a buffer. It is especially preferred to use a buffer that functions at pH 5.0-9.0 to allow the luminescence activity of the calcium-binding photoprotein to be maximized. The buffer includes, for example, phosphate buffer, Tris-HCl buffer, Good buffer, HEPES buffer, citrate buffer, tetraborate buffer, succinate buffer, diethylbarbituric acid buffer, and MOPS buffer.

Furthermore, in order to prevent contamination of calcium, the buffer preferably contains a chelating agent. The chelating agent can be any polydentate ligand which is capable of forming a chelate compound with calcium ion. The chelating agent includes, for example, ethylenediamine tetraacetic acid, hydroxyethylethylenediaminetriacetic acid, dihydroxyethylethylenediaminediacetic acid, trans-1,2-diaminocyclohexane-N,N,N',N'-tetraacetic acid, 1,3-propanediaminetetraacetic acid, diethylenetriaminepentaacetic acid, triethylenetetraminehexaacetic acid, nitrilotriacetic acid, sodium gluconate, hydroxyethyliminodiacetic acid, glycoletherdiaminetetraacetic acid, L-aspartic acid-N,N-diacetic acid, dicarboxymethylglutamic acid tetra-sodium salt, dihydroxyethylglycine, aminotrimethylenephosphonic acid, hydroxyethane phosphonic acid, and salts thereof.

Among the chelating agents, considering the stability constant of chelation with calcium, ethylenediamine tetraacetic acid, glycoletherdiaminetetraacetic acid, diethylenetriaminepentaacetic acid, trans-1,2-diaminocyclohexane-N,N,N',N'-tetraacetic acid, and salts thereof are preferred, and ethylenediamine tetraacetic acid and salts thereof (sometimes called EDTA) are especially preferred.

If there is no adverse impact on the luminescence activity, various salts, such as sodium chloride or ammonium sulphate can be contained in the solution of the peptide from fish.

3) Mixing of the Two Solutions

The protein composition of the present invention can be obtained by mixing the two solutions above. The mixing ratio of the two solutions is not particularly limited, and is preferably adjusted such that the weight ratio of the peptide from fish and the calcium-binding photoprotein is finally in the ranges described above.

4) Lyophilizing

The protein composition of the present invention has excellent protein stability; thus, the function of the protein can be well maintained even under lyophilizing conditions.

The method for lyophilizing is not particularly limited, and can be a conventional method. Specifically, the liquid protein composition is discharged into a vessel, such as a glass bottle and placed resting in a freezer, or immersed in a cooled refrigerant or liquid nitrogen and dried with a freeze dryer after the mixed solution is frozen, to get the desired lyophilized material.

3. Method for Stabilizing a Protein

The method for stabilizing a protein is characterized by contacting the protein stabilizer of the present invention with the protein.

The object of the stabilization method of the present invention, i.e., the protein, can be any one of the proteins described above.

The so-called "contact" refers to allowing the protein stabilizer of the present invention and the object of stabilization, i.e., the protein, to be in the same system, which includes adding the stabilizer into the vessel containing the protein, adding the protein into the vessel containing the stabilizer, and mixing the stabilizer and the protein, and so on.

Herein, the stabilizer and the protein can be in any form of liquid, solid, or powder. Preferably, one or both of the stabilizer and the protein is/are in liquid form, so that they can tightly contact with each other.

Furthermore, as described above, the protein stabilizer of the present invention exhibits excellent stabilization effect even when the protein is lyophilized. Therefore, in view of having no adverse impact on the function of the protein even for long-term storage at room temperature or in refrigeration or for long-term transportation at room temperature, the method for stabilizing a protein of present invention is effective when it is necessary to lyophilize the protein.

4. Uses of the Protein Stabilizer and the Protein Composition of the Present Invention The applications of the protein stabilizer and the protein composition of the present invention are not particularly limited. For example, with the calcium-binding photoprotein being prevented from losing its luminescence activity when the protein is stored for long term at refrigeration temperature of 4° C.-10° C. to room temperature, the types of application include, for example, a probe for signal detection in immunoassay frequently used in clinical examination.

Furthermore, the luminescent kit for the field of amusement or relaxation can also be stored in a common household refrigerator or at room temperature without losing luminescence activity; thus, this luminescent kit is suitable for the intended use.

The kit of the present invention contains the protein composition of the present invention. The substances contained in the kit, besides the protein composition, are not particularly limited and include for example, biotin, avidin, streptavidin, and antibody, and can be produced with general materials and methods. Further, the kit of the present invention can also contain, for example, sample tube, plate, instructions for users of the kit, solution, buffer, reagent, sample suitable for standardization, or a control sample.

Furthermore, the calcium-binding photoprotein can be labelled with biotin, avidin, streptavidin, and antibody and the like.

For application in the field of amusement or relaxation, the kit of the present invention can also contain, for example, flavoring, preservative agents, surfactant, sugar, organic acids, amino acids, and protein. The kit of the present invention can be manufactured with general materials and methods. Furthermore, the kit of the present invention can also contain, for example, a sample tube, instructions for users of the kit, a solution, buffer, and reagent.

Hereinafter, the present invention is described in detail with reference to the following embodiments, but the present invention is not limited to the following embodiments. Furthermore, unless otherwise stated, "%" in the embodiments refers to wt %.

EMBODIMENT

Example 1

Confirmation of Stabilizer Effect of Peptide from Fish on Lyophilizing of Aequorin (1) Preparation of Lyophilized Sample To 792 µl of solutions containing 1%, 0.1%, 0.01% Marine Collagen Oligo CF (having a weight average molecular weight of 1,000, manufactured by Chisso Corporation) in 10 mM EDTA, 50 mM Tris-HCl (pH 7.6) (hereinafter, sometimes called "dilution"), 8 µl of aequorin solution (1.5 mg/ml) in 50 mM Tris-HCl (pH 7.6) containing 1.2 M ammonium sulphate and 10 mM EDTA was added respectively, to make aequorin dilutions having a final concentration of 15 µg/ml. 200 µl of the obtained aequorin dilutions were charged into eppendorf tubes respectively, and lyophilized overnight with a freeze dryer (FDU-2100, manufacture by Tokyo Rikakikai Co., Ltd.) after opening a hole on the cover.

(2) Determination of Luminescence Activity of Aequorin

After lyophilizing, 200 µl of 50 mM Tris-HCl (pH 7.6) containing 10 mM EDTA was added into the obtained lyophilized material, such that the material was re-dissolved and made into an aequorin dilution again. Then, 2 µl of the aequorin dilution before and after lyophilizing were added into a plastic tube respectively, and 50 mM Tris-HCl (pH 7.6) containing 50 mM calcium chloride was injected, and then, the luminescence intensity was measured with a luminometer (AB2200, manufacture by Atto Corporation). The results are shown in Table 1.

Further, the luminescence intensity was measured again according to the method described above, except for using 1% BSA (manufactured by Sigma Company) in 10 mM EDTA, 50 mM Tris-HCl (pH 7.6) instead of the dilution described above, and the results are shown in Table 1. Also, the luminescence intensity was measured again according to the method described above, except for using 50 mM Tris-HCl (pH 7.6) solution containing 10 mM EDTA without any proteins instead of the dilution, as control, and the results are shown in Table 1.

TABLE 1

| Test material | Concentration (%) | luminescence intensity (Imax, rlu) Before lyophilizing | luminescence intensity (Imax, rlu) After lyophilizing | Weight percentage of change in luminescence intensity (%) |
|---|---|---|---|---|
| Marine Collagen | 1 | 110,420 | 119,194 | 107.9 |
|  | 0.1 | 134,355 | 119,824 | 89.2 |
| Oligo CF | 0.01 | 132,181 | 101,269 | 76.6 |
| BSA | 1 | 103,329 | 102,398 | 99.1 |
| Control | — | 101,235 | 69,549 | 68.7 |

In the presence of Marine Collagen Oligo CF, it is confirmed when compared with the control sample that, the luminescence activity of aequorin is maintained, and when the dilutions containing Marine Collagen Oligo CF at a weight percentage of 0.1% and a weight percentage of 1% are used, about higher than or equal to 90% of the activity is maintained. They exert equal stabilization effect on lyophilizing as BSA. Further, "%" of "weight percentage of change in luminescence intensity (%)" in Table 1 refers to the change of the luminescence intensity of aequorin after lyophilizing with respect to the luminescence intensity of aequorin before lyophilizing.

Example 2

Confirmation of stabilization effect in storage at 4° C. after re-dissolution of the lyophilized sample The re-dissolved aequorin dilutions of Example 1 were directly stored at 4° C., and the luminescence intensity was measured after 7 days and 14 days according to the method (2) of Example 1, to confirm the respective stabilization effect. The results are shown in Table 2.

TABLE 2

| Test material | Concentration (%) | Weight percentage of change in luminescence intensity (%) 0 day | 7 days | 14 days |
|---|---|---|---|---|
| Marine Collagen | 1 | 100 | 102 | 83 |
|  | 0.1 | 100 | 106 | 101 |
| Oligo CF | 0.01 | 100 | 99 | 87 |
| BSA | 1 | 100 | 102 | 97 |
| Control | — | 100 | 94 | 79 |

In the presence of Marine Collagen Oligo CF, it is confirmed when compared with the control sample that, the luminescence activity of aequorin is maintained. Even when the calcium-binding protein is stored cold in solution form, Marine Collagen Oligo CF still exerts its stabilization effect.

APPLICABILITY IN INDUSTRY

The protein stabilizer in the present invention can be used as a stabilizer of proteins, especially as a stabilizer for storage in lyophilized form and for cold storage in solution form.

What is claimed is:

1. A method for stabilizing a protein, comprising:
   allowing a peptide obtained by hydrolyzing collagen or gelatine from fish and a calcium-binding photoprotein to be in the same system, wherein the peptide is derived from at least one of the following fish species: sardine, saucy, sparid, salmon, herring, or carp; and
   lyophilizing the system.

2. The method for stabilizing a protein according to claim 1, wherein the calcium-binding photoprotein is selected from one or more of aequorin, obelin, clytin, mitrocomin, mineopsin, and bervoin.

3. The method for stabilizing a protein according to claim 1, wherein a weight average molecular weight of the peptide from the fish is in a range of 500-3,000.

4. The method for stabilizing a protein according to claim 1, wherein a weight ratio of the peptide from the fish and the protein (peptide from fish/protein) is in a range of 10/1-10000/1.

* * * * *